(12) United States Patent
Oda et al.

(10) Patent No.: US 7,467,547 B2
(45) Date of Patent: Dec. 23, 2008

(54) FLUID-MEASURING DEVICE AND FLUID-MEASURING METHOD

(75) Inventors: Seiji Oda, Shizuoka (JP); Yasuhiro Okamoto, Shizuoka (JP); Osamu Kimura, Shizuoka (JP); Mitsuyoshi Anzai, Shizuoka (JP); Hidefumi Ushijima, Shizuoka (JP)

(73) Assignee: Yazaki Corporation, Tokyo (JP)

( * ) Notice: Subject to any disclaimer, the term of this patent is extended or adjusted under 35 U.S.C. 154(b) by 162 days.

(21) Appl. No.: 11/602,242

(22) Filed: Nov. 21, 2006

(65) Prior Publication Data
US 2007/0116083 A1 May 24, 2007

(30) Foreign Application Priority Data
Nov. 21, 2005 (JP) ............................. 2005-336383

(51) Int. Cl.
*G01F 1/68* (2006.01)
(52) U.S. Cl. .................................. 73/204.23
(58) Field of Classification Search .............. 73/204.23, 73/204.26, 204.25, 204.22; 123/494
See application file for complete search history.

(56) References Cited
U.S. PATENT DOCUMENTS
5,708,205 A * 1/1998 Yamada et al. ............ 73/204.26
6,357,294 B1 * 3/2002 Nakada .................... 73/204.26
6,516,785 B1 * 2/2003 Nakada et al. ............. 123/494

FOREIGN PATENT DOCUMENTS
JP 2001-12988 1/2001

* cited by examiner

*Primary Examiner*—Jewel Thompson
(74) *Attorney, Agent, or Firm*—Kratz, Quintos & Hanson, LLP

(57) ABSTRACT

A fluid-measuring device intermittently drives a heater during a measurement period and receives outputs of the lateral side temperature sensors as lateral side temperature signals upon non-driving whenever the heater stops heating during a measuring period. Then, the fluid-measuring device receives outputs of the lateral side temperature sensors in response to the heating of the heater 4 as lateral side temperature signals upon driving corresponding to the lateral side temperature signals upon non-driving. The fluid-measuring device also receives upstream and downstream side temperature signals outputted from upstream and downstream side temperature sensors corresponding to the lateral side temperature signals upon driving. The fluid-measuring device detects physical properties data of the fluid on the basis of the lateral side temperature signal upon non-driving and the lateral side temperature signal upon driving. The fluid-measuring device corrects the upstream and downstream side temperature signals on the basis of the physical properties data. The fluid-measuring device detects a temperature profile varied owing to the velocity of the fluid on the basis of the corrected upstream and downstream side temperature signals, and calculates the flow rate of the fluid.

3 Claims, 9 Drawing Sheets

FLUID-MEASURING DEVICE AND FLUID-MEASURING METHOD

CROSS REFERENCE TO RELATED APPLICATIONS

This application is on the basis of Japanese Patent Application No. 2005-336383, the contents of which are hereby incorporated by reference.

BACKGROUND OF THE INVENTION

1. Field of the Invention

The present invention relates to a fluid-measuring device and a fluid-measuring method, in particular, for measuring a flow of a gas, water, or the like with a flow sensor.

2. Description of the Related Art

A fluid-measuring device using a thermal flow sensor is well known for measuring a flow of a gas, water, or the like. Such a flow sensor utilizes a principle that a heater having a higher temperature than the fluid is disposed in the flow of the fluid, and a temperature profile of the fluid heated by the heater changes as a velocity of the flow of the fluid increases.

Japanese published patent application No. 2001-12988 discloses such a flow sensor. This conventional thermal flow sensor will be explained with reference to FIGS. 6 and 7.

In FIG. 6, a flow sensor 1 includes a silicon substrate 2, a diaphragm 3, micro heater 4 composed of platinum or the like formed on the diaphragm 3, a downstream side thermopile 5 disposed downstream of the micro heater 4 and formed on the diaphragm 3, power source terminals 6A, 6B for supplying driving current from a not shown power source to the micro heater 4, an upstream side thermopile 8 disposed upstream of the micro heater 4 and formed on the diaphragm 3, first output terminals 9A, 9B for outputting upstream side thermal signal from the upstream side thermopile 8, and second output terminals 7A, 7B for outputting a downstream side thermal signal from the downstream side thermopile 5.

Further, the flow sensor 1 includes: a right side thermopile 11 disposed substantially perpendicular to a flow of the fluid with respect to the micro heater 4 (a direction from P to Q), detecting physical properties data of the fluid, and outputting a right side thermal detecting signal (corresponding to a third thermal detecting signal); third output terminals 12A, 12B outputting the right side thermal detecting signal from the right side thermopile 11; a left side thermopile 13 disposed substantially perpendicular to the flow of the fluid with respect to the micro heater 4, detecting physical properties data of the fluid, and outputting a left side thermal detecting signal (corresponding to a third thermal detecting signal); fourth output terminals 14A, 14B outputting the left side thermal detecting signal from the left side thermopile 13; resistor 15, 16 for attaining a fluid temperature; and output terminals 17A, 17B for outputting a fluid temperature signal from the resistor 15, 16. The right and left side thermopiles 11, 13 compose a thermal sensor.

Each of the upstream side thermopile 8, the downstream side thermopile 5, the right side thermopile 11, and the left side thermopile 13 is composed of a thermocouple. This thermocouple is composed of p++-silicon and aluminum, and has a cold junction 5b, 8b and a hot junction 5a, 8a. When detecting heat, a thermal electromotive force is generated owing to a temperature difference between the cold junction 5b, 8b and the hot junction 5a, 8a so that the thermocouple outputs a temperature detecting signal.

Further, as shown in FIG. 7, the diaphragm 3 is formed on the silicon substrate 2. The hot junctions of the micro heater 4, the upstream side thermopile 8, the downstream side thermopile 5, the right side thermopile 11, and the left side thermopile 13 are formed on the diaphragm 3.

In the flow sensor 1, when the micro heater starts heating with the driving current from the outside, the heat generated by the micro heater 4 is transferred to the hot junctions 5a, 8a of the downstream side thermopile 5 and the upstream side thermopile 8 through the fluid. Because the cold junctions 5b, 8b are on the silicon substrate, they are at the substrate temperature. The hot junctions 5a, 8a are on the diaphragm 3 and heated by the transferred heat, and the temperature of the hot junctions 5a, 8a are hotter than the silicon substrate. Therefore, each thermopile generates the thermal electromotive force owing to the temperature difference between the hot junction 5a, 8a and the cold junction 5b, 8b, and outputs the temperature detecting signal.

The heat transferred by the fluid is transferred to the thermopiles by a synergistic effect of a thermal diffusion and a drift of the fluid from P to Q. Namely, when there is no drift, owing to the thermal diffusion, the heat is transferred to the upstream side thermopile 8 and the downstream side thermopile 5 equally, and a difference between an upstream side thermal signal from the upstream side thermopile 8 and a downstream side thermal signal from the downstream side thermopile 5 is zero.

On the other hand, when the drift is occurred, quantity of the heat transferred to the hot junction 5a of the downstream side thermopile 5 is increased, and quantity of the heat transferred to the hot junction 8a of the upstream side thermopile 8 is decreased. Therefore, the difference signal between the downstream side thermal signal and the upstream side thermal signal is a positive value corresponding to the velocity of the fluid.

When the micro heater 4 starts heating with the driving current, the heat generated by the micro heater 4 is transferred to the right side thermopile 11 disposed substantially perpendicular to the direction of the drift of the fluid with respect to the micro heater 4 by the thermal diffusion effect of the fluid without an influence of the drift of the fluid. The same heat is transferred to the left side thermo pile 13 disposed substantially perpendicular to the direction of the drift of the fluid with respect to the micro heater 4. Accordingly, the right side temperature detecting signal outputted from the third output terminals 12A, 12B owing to the electromotive force of the right side thermopile 11, and/or the left side temperature detecting signal outputted from the fourth output terminals 14A, 14B owing to the electromotive force of the left side thermopile 13 are corresponding to physical properties of the fluid such as thermal diffusion coefficient determined by conduction of heat, thermal diffusion, specific heat and the like. The proper process can attain physical properties.

A size of thermal diffusion constant also influences the upstream side temperature signal outputted by the upstream side thermopile 8 and the downstream side temperature signal outputted by the downstream side thermopile 5. They are changed similar to the left and right side thermopiles. Therefore, in principle, a correct flow rate of fluid having various thermal diffusion constants, namely, every fluid can be calculated by subtracting the right and/or left thermopile output from the upstream side temperature signal, the downstream side temperature, or the difference between them.

Therefore, a not-shown flow meter realizes a high accuracy measurement by calculating the physical properties of the fluid on the basis of the left and right side temperature detecting signals, and correcting the difference between the upstream and downstream side temperature signals with the physical properties.

However, such a flow sensor 1 has a problem that in spite of a correction corresponding to the physical properties of the fluid, reproducibility of a measurement is not good. In particular, in a case of measuring of large amount, namely, rapid drift, the reproducibility is worse. This is one reason of limiting a measuring range of the flow meter.

We found that the output of the flow meter changes even when the current is not supplied to the micro heater 4, namely, the flow sensor 1 is not driven. The detail will be explained as follows.

The flow rate is measured per 100 L/min in a standard condition.

A unit of an instrumental error as shown by a vertical axis in FIG. 9 is % RD (% of Reading). For example, in a meter having a maximum flow of 100 L/min, when the meter measures 10 L/min and the output is 9 L/min, the instrumental error is −10% RD. At this time, a tolerance is −1% (FS).

As shown in FIG. 8, when the thermal difference is zero and the heater is not heated, a temperature sensor output is V0. When the heater is heated, the temperature sensor output is V2. In this case, when a gas temperature becomes higher than a housing temperature, the output V0 turns to V1 and the output V2 turns to V3. However, because the flow sensor 1 is constantly powered, the output of V0 and V3 cannot be measured. The output V2 changes to V3.

FIG. 9 shows a measuring result of the output of the flow sensor 1 shown in FIG. 6. The instrumental errors are about +20% RD at the temperature difference of −30 degree, and about −20% RD at the temperature difference of +30 degree.

In the flow sensor 1 of FIG. 6, because the outputs of the upstream side thermopile 8 and the downstream side thermopile 5 caused by the temperature difference of the gas and the sensor body are substantially the same, the measurement of the differential output is automatically canceled. However, outputs of the left and right side thermopiles cannot be canceled because the differential output is not taken out. Because an accurate measurement cannot be taken if the differential output of the upstream side thermopile 8 and the downstream side thermopile 5 is corrected by the outputs of the right side thermopile 11 and the left side thermopile 13, the output accuracy of the flow sensor 1 becomes worse. Thus, the output of the flow sensor 1 is varied in proportion to the temperature difference between the gas and the sensor body.

Accordingly, an object of the present invention is to provide a fluid-measuring device and a fluid-measuring method for increasing a measuring accuracy without increasing complexity of a flow sensor structure.

SUMMARY OF THE INVENTION

In order to attain the object, according to the present invention, there is provided a fluid-measuring device using a flow sensor 1 including:

a heater 4 for heating a fluid flowing in a flow path and generating a specific temperature profile;

an upstream side temperature sensor 8 for detecting temperature of the fluid at the upstream of the flow path with respect to the heater 4, and outputting an upstream side temperature signal;

a downstream side temperature sensor 5 for detecting the temperature of the fluid at the downstream of the flow path with respect to the heater 4, and outputting a downstream side temperature signal; and lateral side temperature sensors 11, 13 disposed at a direction substantially perpendicular to a flow of the fluid for detecting the temperature of the fluid and outputting lateral side temperature signals, said fluid-measuring device including:

a heater controller 41a for intermittently driving the heater 4 for a measuring interval from a start of measuring the flow rate to the end of measuring;

a lateral side temperature signal upon non-driving receiving member 41b for receiving a lateral side temperature signal outputted from the lateral side temperature sensor 11, 13 whenever the heater 4 stops driving by a control of the heater controller 41a as a lateral side temperature signal upon non-driving;

a lateral side temperature signal upon driving receiving member 41c for receiving a lateral side temperature signal outputted from the lateral side temperature sensor 11, 13 in response to the driving of the heater 4 controlled by the heater controller 41a the after the lateral side temperature signal upon non-driving receiving member 41b receives the lateral side temperature signal upon non-driving as a lateral side temperature signal upon driving corresponding to the lateral side temperature signal upon non-driving received by the lateral side temperature signal upon non-driving receiving member 41b;

a physical properties data detecting member 41d for detecting physical properties data indicating physical properties of the fluid corresponding to the thermal profile in the substantially perpendicular direction on the basis of the lateral side temperature signal upon non-driving received by the lateral side temperature signal upon non-driving receiving member 41b and the lateral side temperature signal upon driving received by the lateral side temperature signal upon driving receiving member 41c;

a temperature signal receiving member 41e for receiving the upstream side temperature signal outputted by the upstream side temperature sensor 8 and the downstream side temperature signal outputted by the downstream side temperature sensor 5 corresponding to the lateral side temperature signal upon driving received by the lateral side temperature signal upon driving receiving member 41c when the heater 4 is driven by a control of the heater controller 41a;

a correcting member 41f for correcting the upstream and downstream side temperature signals received by the temperature signal receiving member 41e on the basis of the physical properties data detected by the physical properties data detecting member 41d; and a flow rate calculating member 41g for detecting the temperature profile varied corresponding to the velocity of the fluid on the basis of the upstream and downstream side temperature signals corrected by the correcting member 41f and calculating the flow rate of the fluid on the basis of the detected temperature profile.

Preferably, the fluid-measuring device further includes a temperature signal upon non-driving receiving member 41h for receiving the upstream side temperature signal outputted by the upstream side temperature sensor 8 and the downstream side temperature signal outputted by the downstream side temperature sensor 5 corresponding to the lateral side temperature signal upon non-driving received by the lateral side temperature signal upon non-driving receiving member 41b when the heater is not driven by the control of the heater controller 41a, and the correcting member 41f corrects the upstream and downstream side temperature signals received by the temperature signal receiving member 41e on the basis of the upstream and downstream side temperature signals received by the temperature signal upon non-driving receiving member 41h, and corrects the corrected upstream and downstream side temperature signals on the basis of the physical properties data detected by the physical properties data detecting member 41d.

According to another aspect of the invention, there is provided a fluid-measuring method for measuring a flow rate of the fluid with a flow sensor 1, said flow sensor 1 including:

a heater 4 for generating a specific temperature profile by heating the fluid flowing in a flow path;

an upstream side temperature sensor 8 for detecting a temperature of the fluid at the upstream side of the flow path with respect to the heater 4, and outputting an upstream side temperature signal;

a downstream side temperature sensor 5 for detecting the temperature of the fluid at the downstream side of the flow path with respect to the heater 4, and outputting an downstream side temperature signal; and a lateral side temperature sensor 11, 13 disposed substantially perpendicular to a flow direction of the fluid for detecting the temperature of the fluid and outputting the lateral side temperature signal, said fluid-measuring method including the steps of:

controlling the heater 4 intermittently driving during a measuring period from a start of the measurement of the flow rate to an end, receiving the lateral side temperature signal outputted from the lateral side temperature sensor 11, 13 as a lateral side temperature signal upon non-driving during the measuring period, whenever the heater 4 stops driving;

receiving the lateral side temperature signal outputted from the lateral side temperature sensor 11, 13 in response to the driving of the heater 4 as a lateral side temperature signal upon driving corresponding to the lateral side temperature signal upon non-driving;

receiving the upstream side temperature signal outputted from the upstream side temperature sensor 8 and the downstream side temperature signal outputted from the downstream side temperature sensor 5 corresponding to the lateral side temperature signal upon driving;

detecting a physical properties data for indicating physical properties of the fluid in the substantially perpendicular direction in response to the temperature profile on the basis of the lateral side temperature signal upon non-driving the lateral side temperature signal upon driving;

correcting the upstream and downstream side temperature signals on the basis of the physical properties data;

detecting the temperature profile changed corresponding to the velocity of the fluid on the basis of the corrected upstream and downstream side temperature signals; and calculating the flow rate of the fluid on the basis of the detected temperature profile.

These and other objects, features, and advantages of the present invention will become more apparent upon reading of the following detailed description along with the accompanied drawings.

DETAILED DESCRIPTION OF THE PREFERRED EMBODIMENTS

An embodiment of a fluid-measuring device according to the present invention using a flow sensor 1 (see FIG. 6) which is already explained will be explained with reference to FIGS. 2 to 5.

Figure 1:
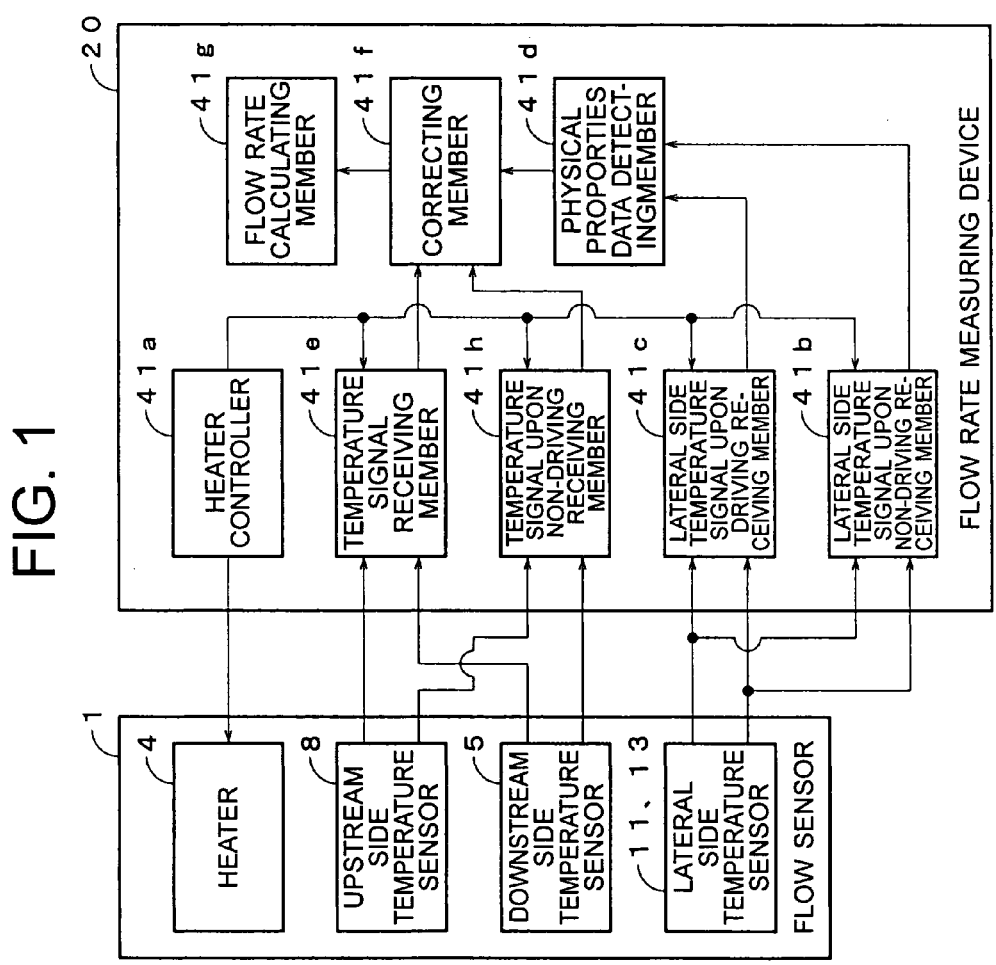
FIG. 1 is a schematic diagram showing a basic configuration of the fluid-measuring device according to the present invention.
Figure 2:
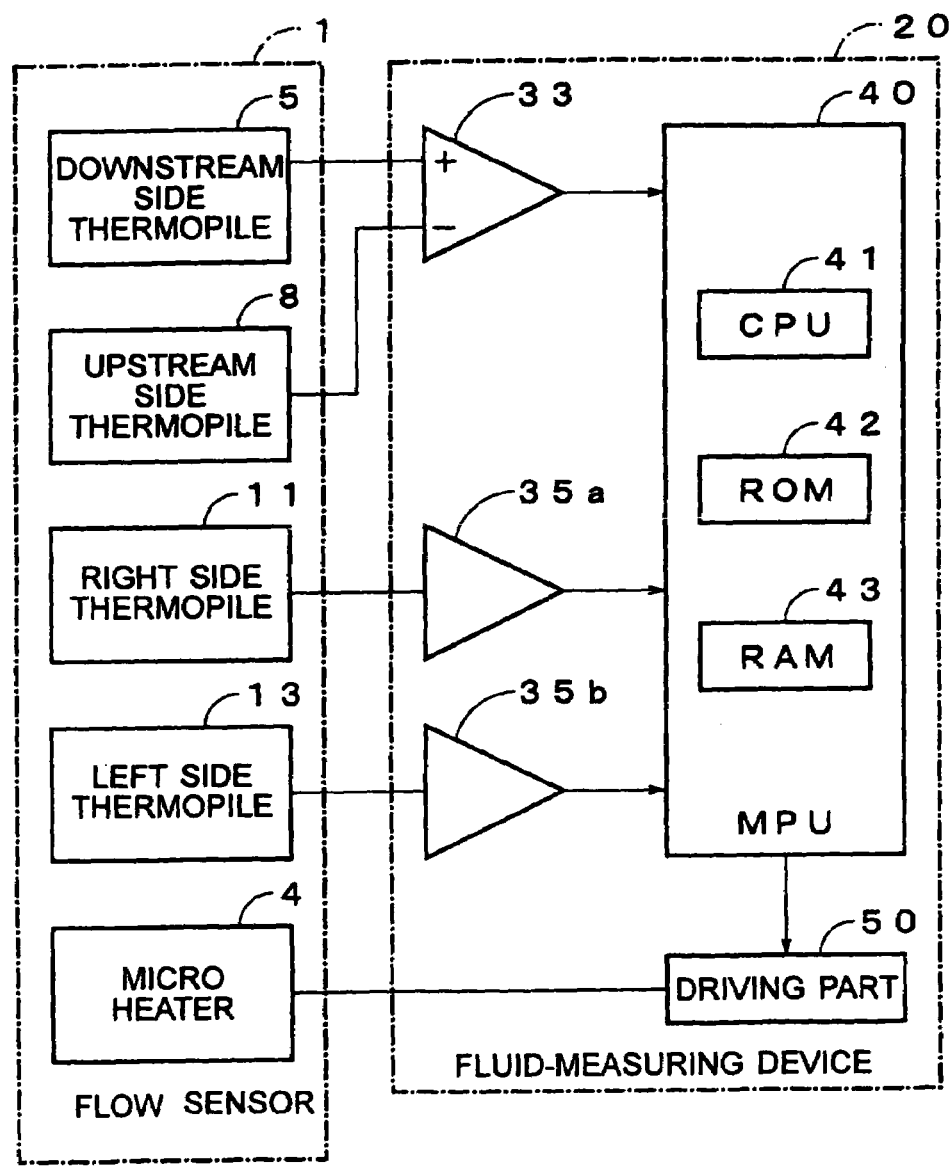
FIG. 2 is a block diagram of the fluid-measuring device using a flow sensor.

In FIG. 2, a fluid-measuring device 20 according to the present invention measures a flow rate of a gas as a fluid using the flow sensor 1. The flow sensor 1 includes:

a micro heater 4 for generating a specific temperature profile by heating the fluid owing to the driving of the fluid-measuring device 20;

a upstream side thermopile (upstream side temperature sensor) 8 for detecting the temperature of the fluid at the upstream of the flow path with respect to the micro heater 4, and outputting the upstream side temperature signal;

a downstream side thermopile (downstream side temperature sensor) 5 for detecting the temperature of the fluid at the downstream of the flow path with respect to the micro heater 4, and outputting the downstream side temperature signal; and left and right side thermopiles (lateral side temperature sensor) 11, 13 disposed in a direction substantially perpendicular to the flow direction for detecting the temperature of the fluid and outputting left and right side temperature detecting signals (lateral side temperature signals).

The fluid-measuring device 20 includes: a differential amplifier for amplifying a differential signal between the upstream and downstream side temperature signals outputted from the downstream side thermopile 5 and the upstream side thermopile 8 in the flow sensor 1;

an amplifier 35a for amplifying the right side detecting signal from the right side thermopile 11 in the flow sensor 1;

an amplifier 35b for amplifying the left side detecting signal from the left side thermopile 13 in the flow sensor 1;

a microprocessor (MPU) 40 operating according to a predetermined program; and a driving part 50 controlled by the MPU 40 for driving the micro heater 4. The differential amplifier 33, the amplifiers 35a, 35b, and the driving part 50 are connected to the MPU 40.

As is generally known, the MPU 40 includes a CPU 41, a ROM 42, and a RAM 43.

The ROM 42 stores various programs for making the CPU 41 work as a heater controller, a lateral side temperature signal upon non-driving receiving member, a lateral side temperature signal upon driving receiving member, a physical properties data detecting member, a temperature signal receiving member, a correcting member, a flow rate calculating member, and a temperature signal upon non-driving receiving member.

A differential signal between the upstream and downstream side signals from the downstream side thermopile 5 and the upstream side thermopile 8 is inputted into the CPU 41 through the differential amplifier 33. Incidentally, the differential amplifier 33 is used in this embodiment. However, this invention is not limited to this. For example, the upstream and downstream side signals may be directly inputted into the CPU 41 after the signals are amplified.

The right side temperature-detecting signal from the right side thermopile 11 is inputted into the CPU 41 through the amplifier 35a. The left side temperature-detecting signal from the left side thermopile 13 is inputted into the CPU 41 through the amplifier 35b. Incidentally, in this embodiment, two amplifiers 35a, 35b are used. However, the sum of the two signals can be used.

A driving part 50 is connected to the MPU 40, and has a driving circuit for driving the micro heater 4 in response to a command of the MPU 40.

Next, one example of a flow rate measuring process executed by the CPU 41 of the MPU 40 will be explained with reference to a flowchart in FIG. 3. Incidentally, this flow rate measuring process is continuously carried out while the fluid-measuring device 20 works, and ends corresponding to a shutdown of the fluid-measuring device 20.

Figure 3:
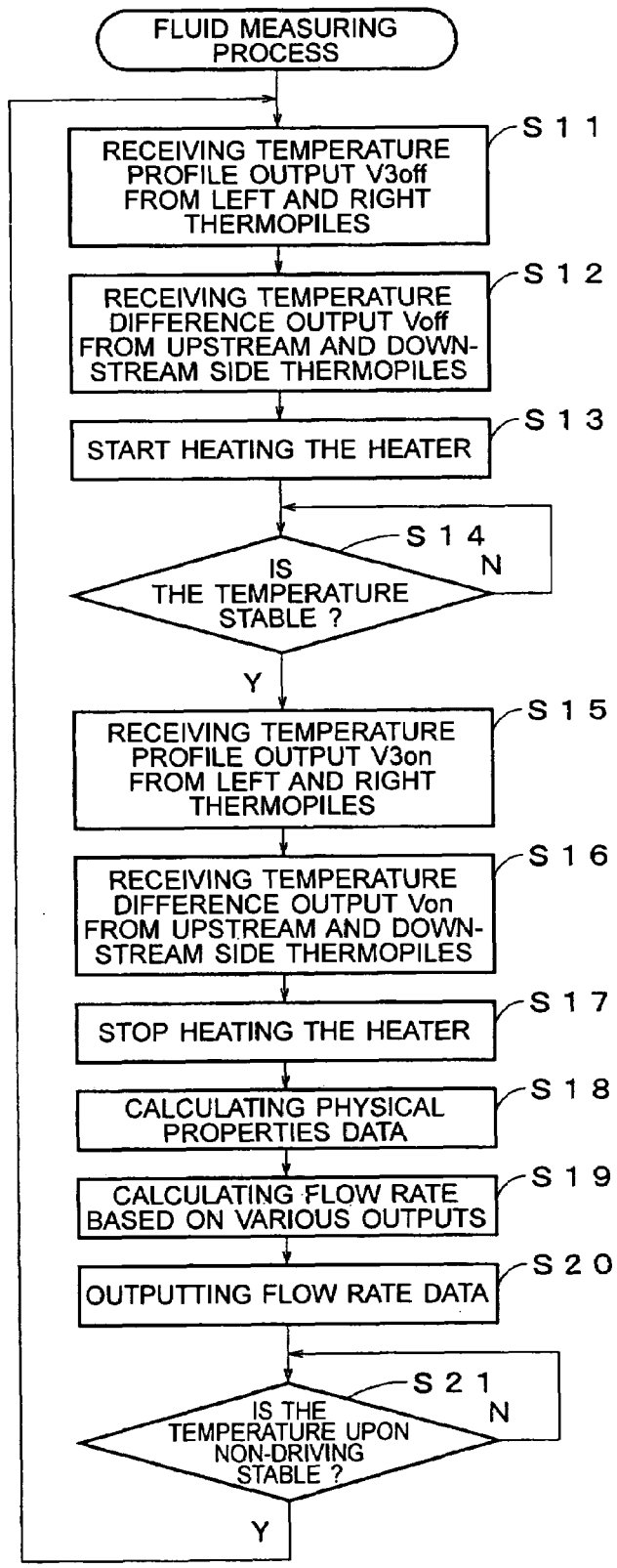
FIG. 3 is a flow chart showing an example of a flow rate measuring process executed by the microcomputer according to the present invention.

As shown in FIG. 3, in step S11 (a lateral side temperature signal upon non-driving receiving step), the left and right side temperature detecting signals are received from the left and right thermopile 13, 11 through the amplifiers 35a, 35b. These signals are stored in the RAM 43 as a temperature profile output upon non-driving V3off, and the process goes to step S12.

In step S12 (a temperature signal receiving upon non-driving step), the differential signal between the upstream and downstream side signals outputted from the upstream and downstream side thermopiles 8, 5 corresponding to the temperature profile output upon non-driving V3off is received through the differential amplifier 33. This signal is stored in the RAM 43 as the temperature difference upon non-driving Voff, and the process goes to step S13.

In step S13 (a heater control step), the driving part 50 is commanded to start heating the micro heater 4, and the process goes to step S14. Corresponding to this command, the driving part supplies a specific voltage to the micro heater 4. Resultingly, a gas surrounding the micro heater 4 is heated and a specific temperature profile is generated.

In step S14, whether the temperature of the micro heater 4 is stable or not is judged. Incidentally, various ways can be used for this judgement. For example, one way is to memorize a predetermined time for the temperature to be stable and to judge with a timer. Another way is to judge with the temperatures using the right side thermopile 11 and the left side thermopile 13.

When the temperature is judged not to be stable ("N" in S14), this process is repeated until the temperature is stable. On the other hand, when the temperature is judged to be stable ("Y" in S14), the process goes to step S15.

In step S15 (lateral side temperature signal upon driving receiving step), the left and right side temperature detecting signals from the left side thermopile 13 and the right side thermopile 11 through the amplifier 35a, 35b are received, and stored in the RAM 43 as the temperature profile upon driving V3on. Then, the process goes to step S16.

In step S16 (temperature signal upon driving receiving step), the differential signal between the upstream and downstream side temperature signals outputted from the upstream side thermopile 8 and the downstream side thermopile 5 corresponding to the temperature profile upon driving V3on are received through the differential amplifier 33, and the differential signal is stored in the RAM 43 as a differential temperature output upon driving Von. Then, the process goes to step S18.

In step S18 (a physical properties data-detecting step, a correction step), by subtracting the temperature profile outputs V3on from V3off, the physical properties data is calculated and stored in the RAM 43. Then, the process goes to step S19. Incidentally, according to the physical properties data, physical property of the fluid can be attained to some degree.

In step S19 (a flow rate calculating step, a correction step), by calculating the temperature profiles Von, Voff in the RAM 43, the physical properties data (V3on−V3off) with a later described flow rate calculating formula, the flow rate per one measurement is calculated and stored in the RAM 43 as a flow rate data. Then, in step S20, the flow rate data is displayed on the predetermined display.

Incidentally, in this embodiment, a calculation program for calculating (Von−Voff)/(V3on−V3off) is previously stored in the ROM 42. However, when the correction of the temperature difference output Von is not necessary, the calculation program for calculating the formula of Von/ (V3on−V3off) may be stored in the RAM 42, and step S12 may be canceled.

In step S21, whether the temperature upon non-driving of the micro heater 4 which is stopped at step S17 is stable or not is judged. Similar to step S14, when the temperature is not stable ("N" in S21), this process is repeated until the temperature is stable. On the other hand, when the temperature is judged stable ("Y" in S21), the process goes back to step S11, and a series of process is repeated. Incidentally, the process may not go back rapidly. The process may go back after a while.

Here, the reason why the above described fluid-measuring device and fluid-measuring method are effective will be explained in comparison with the conventional measuring device and the measuring method.

In the conventional measurement, the micro heater 4 is not driven intermittently. Therefore, the temperature sensor output upon non-driving is not measured. Therefore, the output from the flow sensor 1 is Von/V3on. ON the other hand, the output according to the present invention is Von/(V3on−V3off). If V3off=0, the outputs are equal. However, when the temperature of the fluid is higher than that of the sensor body, the temperature of the diaphragm 3 where the temperature sensor is mounted is increased, and the output V3off is larger than zero. The output V3on also is affected by the increase of the temperature of the diaphragm 3, and the output is V3off higher than that of the zero temperature difference.

Namely, the measuring error caused by the increase of the temperature of the diaphragm 3 can be canceled.

Incidentally, it is similar when the Von becomes Von−Voff. Namely, because the output Von is a difference between the downstream side temperature output and the upstream side temperature output, if the upstream and downstream temperature sensors are strictly symmetric, both output upon non-driving is the same and the correction is unnecessary. However, because such strictly symmetric sensors are hard to produce, a good measuring accuracy can be expected by using Von−Voff.

Next, an example of an operation of the fluid-measuring device 20 will be explained with reference to FIGS. 4 and 5.

When the fluid measurement process described above is executed by the fluid-measuring device 20, a voltage Vth is supplied intermittently to the micro heater 4 of the flow sensor 1 in a predetermined timing of a driving signal G shown by a solid line in FIG. 4A. Then, according to this embodiment, a pulse signal composed of a driving time T1 for applying the voltage Vth to the micro heater 4, and a non-driving time T2 for not applying a voltage controls the micro heater 4 during the measurement time from the start of the gas measurement to the end. Incidentally, in this embodiment, the measuring time is when the fluid-measuring device 20 starts up. However, the present invention is not limited to this.

The driving time T1 is enough time to heat the gas (fluid) to generate the specific temperature profile, and the non-driving time T2 is enough time to return to the normal temperature. Incidentally, there are various ways to control the micro heater 4. For example, the micro heater 4 is intermittently driven according to the predetermined timing from the measurement start to the end.

When the temperature difference between the gas and the sensor body is zero, the signal detected and outputted by the flow sensor 1 corresponding to the driving signal G is indicated by a temperature signal G1. When the temperature difference between the gas and the sensor body is not zero, the signal is $\Delta V$ higher than the temperature signal G1 and indicated by a temperature signal G2.

According to the above, the constant voltage Vth is intermittently applied in the present invention, and is continuously applied in the conventional art. As shown in FIG. 4, outputs from each thermopile is varied in response to the temperature difference between the gas and the sensor body.

Figure 4:
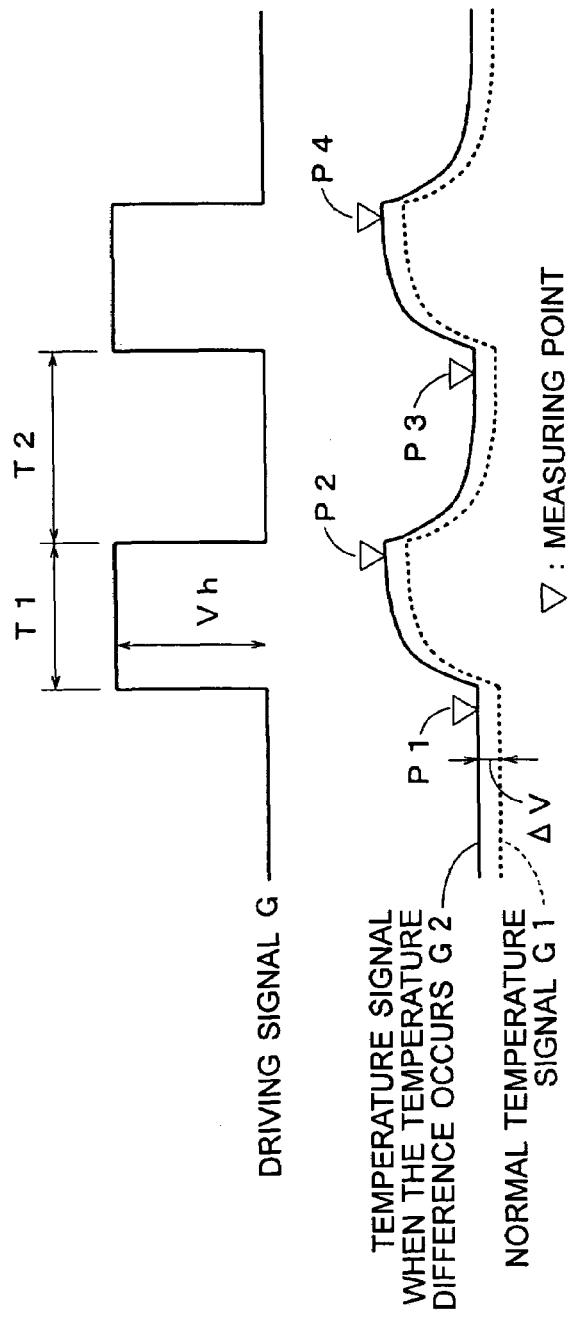
FIGS. 4A and 4B are graphs for explaining an example of a heater-applied voltage and an output of the flow sensor.

With respect to the flow sensor 1, the fluid-measuring device 20 receives the temperature profile output V3off from the right and left side thermopiles 11, 13 and receives the temperature difference Voff from the upstream side thermopile 8 and the downstream side thermopile 5 at the measuring point P1 in FIG. 4 where the voltage Vth is not applied, and then the micro heater starts heating the gas.

At the measuring point P2 in FIG. 4, in a condition that the temperature of the heated gas is stable, the fluid-measuring device 20 receives the temperature profile output V3off from the right and left side thermopiles 11, 13 and receives the temperature difference Voff from the upstream side thermopile 8 and the downstream side thermopile 5, and then the micro heater 4 stops heating the gas.

The fluid-measuring device 20 detects the physical properties data on the basis of the difference between the temperature profile outputs V3on and V3off, calculates the flow rate of the gas using the physical properties data, Von, Voff, and the flow rate calculating formula, and displays the flow rate data.

Then, at the measuring point P3 in FIG. 4, when the temperature upon non-driving is stable, similar to the measuring point P1, the fluid-measuring device 20 receives the temperature profile output V3off and the temperature difference output Voff respectively, and the micro heater 4 starts heating the gas. Then, at the measuring point P4 in FIG. 4, when the temperature of the heated gas is stable, similar to the measuring point P2, the fluid-measuring device 20 receives the temperature profile output V3on, the temperature difference output Voff, respectively, and the micro heater 4 stops heating the gas. Then, the fluid-measuring device 20 detects the physical properties data corresponding to the temperature profile, and calculates the flow rate.

During the gas-measuring period, such a process is repeated, the physical properties data is continuously detected, the upstream and downstream temperature sensor output is corrected with the physical properties data, and the flow rate is calculated.

Figure 5:
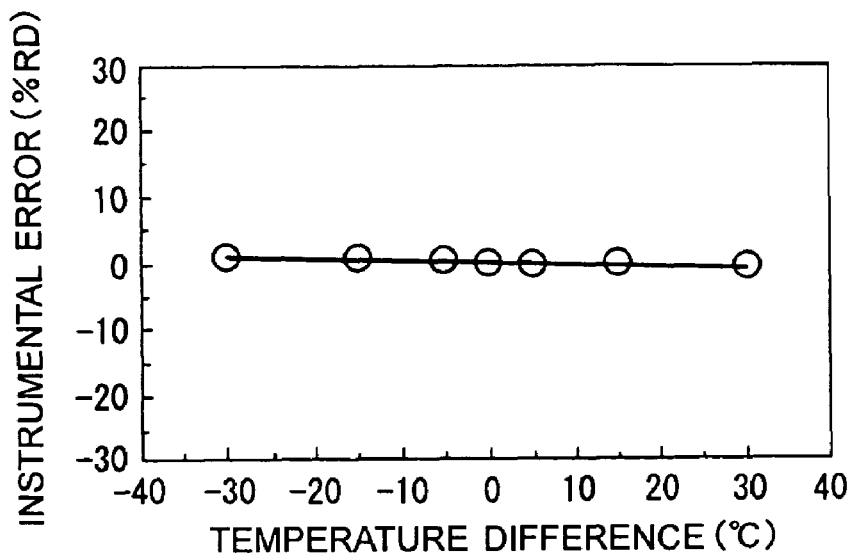
FIG. 5 is a graph showing a relationship between a temperature difference and an instrumental error according to the present invention.
Figure 6:
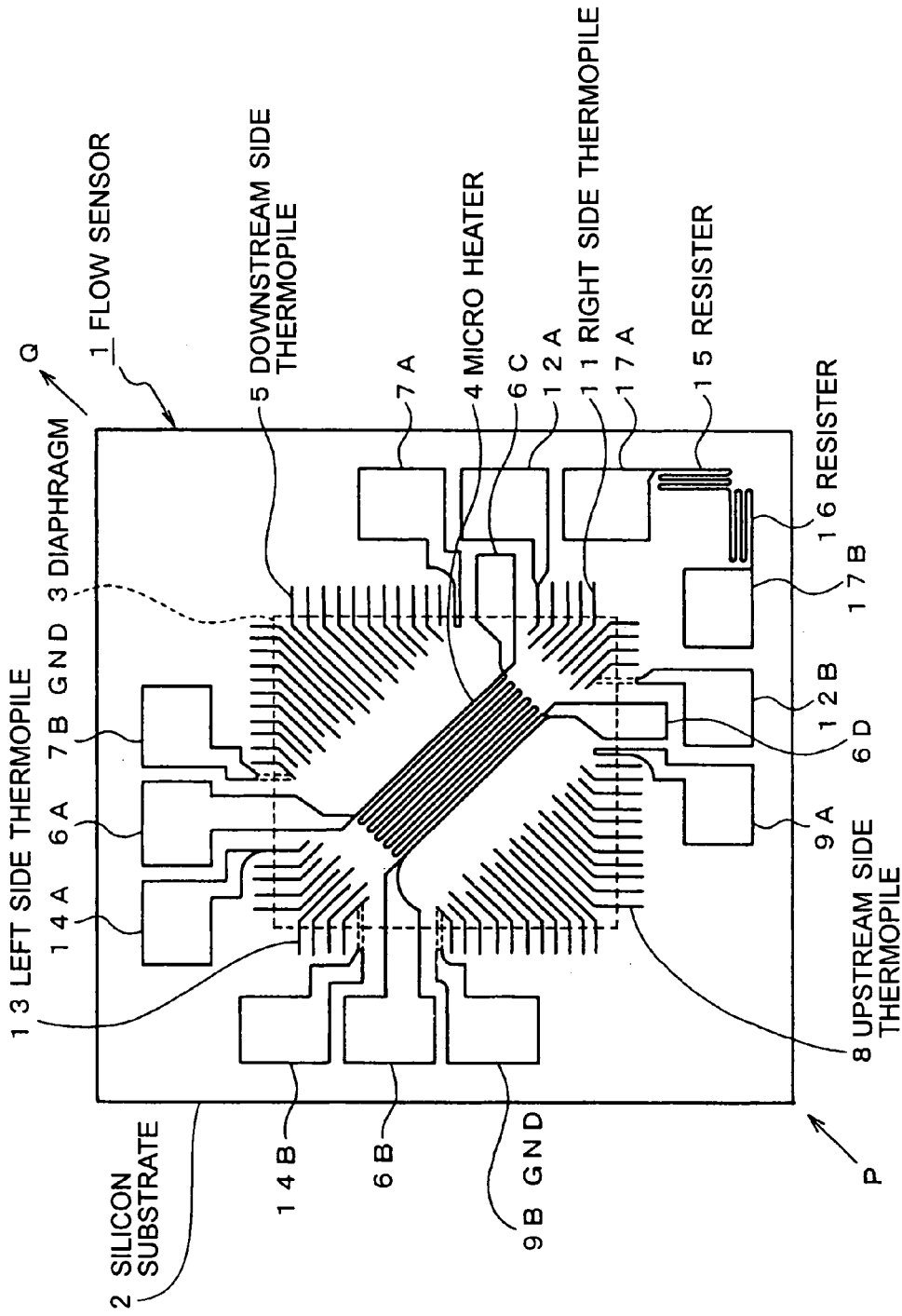
FIG. 6 is a schematic view showing a conventional thermal flow sensor.
Figure 7:
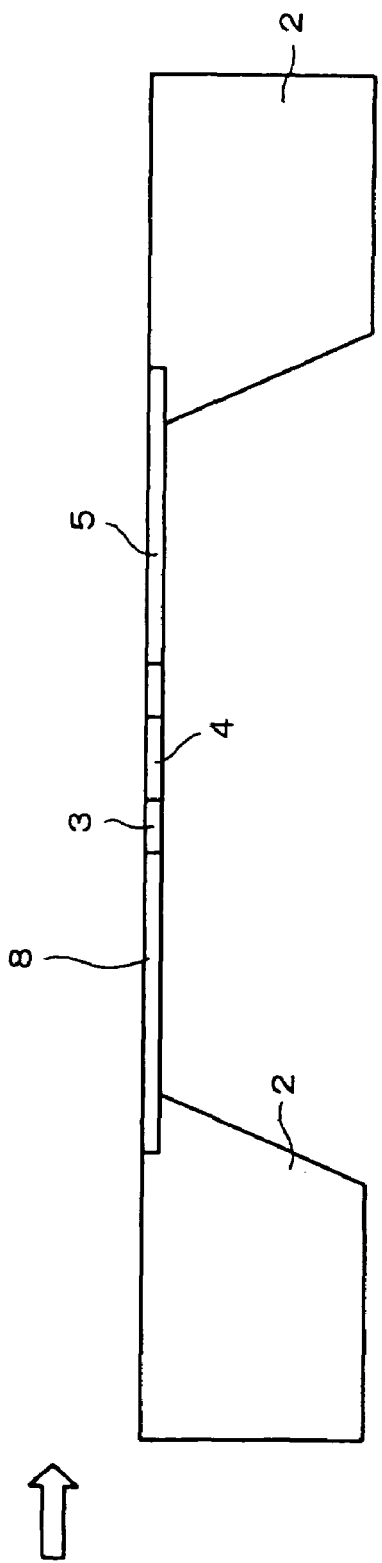
FIG. 7 is a cross sectional view of the flow sensor shown in FIG. 6.
Figure 8:
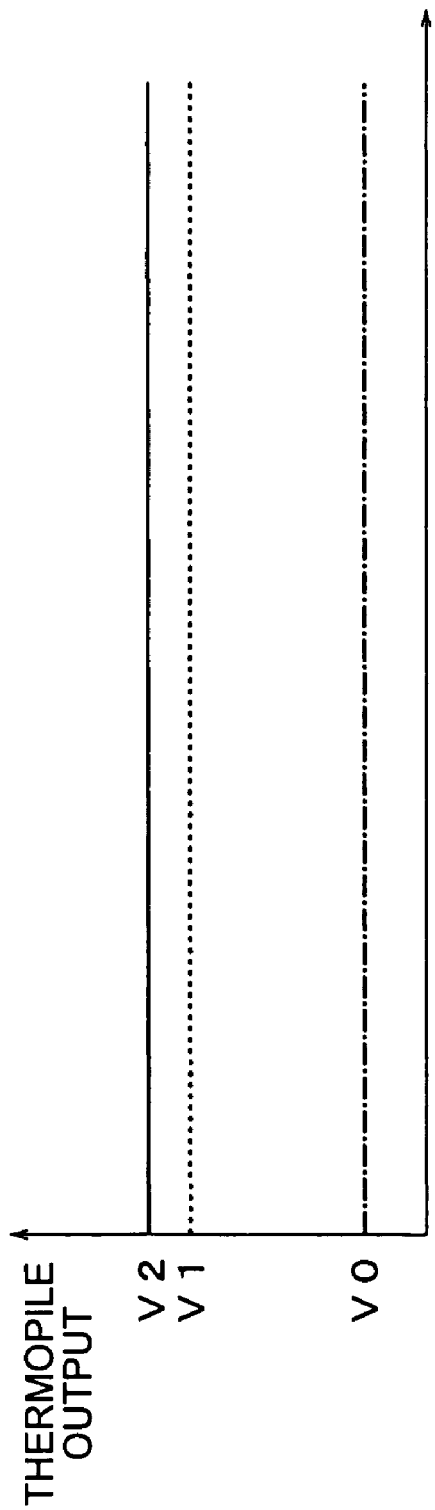
FIG. 8 is a schematic diagram showing the outputs of the thermopile versus temperature difference according to the conventional way.
Figure 9:
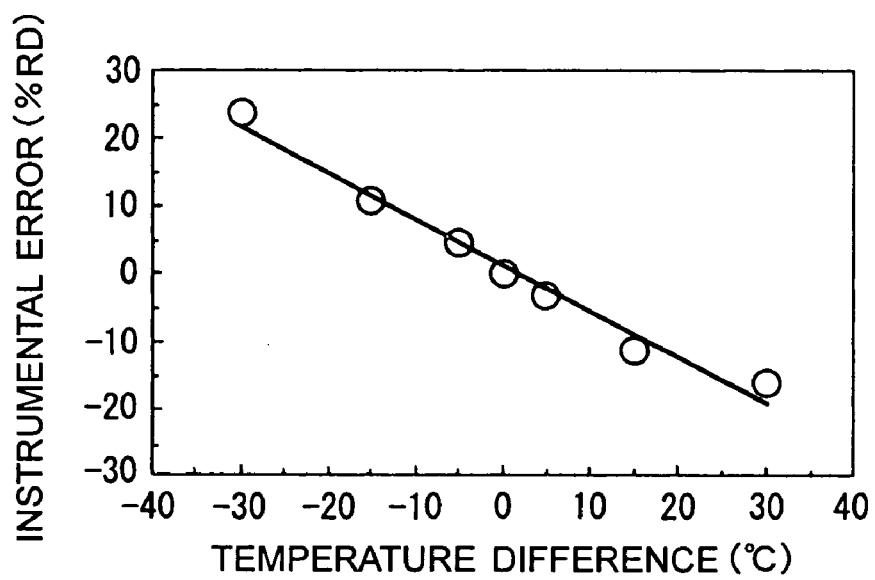
FIG. 9 is a graph showing a relationship of the temperature difference between the fluid temperature measured by the conventional flow sensor and a sensor body temperature, and the instrumental error.

Under the measuring condition described in the description of the related art, the relationship between the temperature difference and the instrumental error is shown in FIG. 5. In detail, when the temperature difference between the sensor body and the gas is varied from about −30 to 30 degrees, the instrumental error is 1% RD at −30 degrees, about 0% RD at −15 degrees, about 0.5% RD at −5 degrees, about 0% RD at 5 degrees, about 0% RD at 15 degrees, about −1% RD at 30 degrees. Namely, the fluid-measuring device 20 according to the present invention cancels the instrumental error caused by the variety of the temperature difference.

According to the fluid-measuring device 20 of the present invention, during the measurement of the fluid, the micro heater 4 is intermittently driven, and whenever the micro heater 4 stops driving, the fluid-measuring device 20 receives the lateral side temperature signal upon non-driving from the left and right thermopiles 13, 11. When the micro heater 4 is driven, the fluid-measuring device 20 receives the lateral side temperature signal upon driving. Based on the lateral side temperature signals, the physical properties data of the fluid corresponding to the temperature profile substantially perpendicular to the flow direction is detected. Based on the upstream and downstream side temperature signals corrected according to the physical properties data, the temperature profile varied corresponding to the velocity of the gas is detected. The flow rate is measured on the basis of the temperature profile. Accordingly, the offset output of the temperature sensor caused by the temperature difference between the sensor body and the fluid is canceled. Therefore, even when the temperature difference between the sensor body and the fluid exists, the output accuracy of the flow sensor is good.

It is achieved only by changing the driving control method with respect to the micro heater 4 of the flow sensor. Therefore, without complicating the structure of the flow sensor, the measuring accuracy with respect to various gases (fluids) is improved. Further, an existing flow sensor 1 can be used for the fluid-measuring device 20. The fluid-measuring device 20 can be made by changing hardware such as some additional switches and changing software for controlling them. Namely, an improvement of the measuring accuracy is achieved with simple changes.

Further, whenever the micro heater stops driving, the fluid-measuring device 20 receives the upstream and downstream temperature signals from the upstream side thermopile 8 and the downstream side thermopile 5, and corrects the upstream and downstream temperature signal. Therefore, one of error factors of the measurement accuracy is further canceled, and the measuring accuracy is further improved.

Incidentally, in the preferred embodiment, members in claims are realized by the MPU 40. However, the present invention is not limited to this. For example, DSP (digital signal processor) or ASIC (application specific IC) can be used.

Incidentally, in the preferred embodiment, the fluid-measuring device 20 is explained. However, the present invention is not limited to this. The fluid-measuring device 20 may be embedded in a gas meter. The fluid-measuring device 20 may be used for measuring water, medicines, or the like.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. A fluid-measuring device using a flow sensor
said flow sensor including:
a heater for heating a fluid flowing in a flow path and generating a specific temperature profile;

an upstream side temperature sensor for detecting temperature of the fluid at the upstream of the flow path with respect to the heater, and outputting an upstream side temperature signal;

a downstream side temperature sensor for detecting the temperature of the fluid at the downstream of the flow path with respect to the heater, and outputting a downstream side temperature signal; and lateral side temperature sensors disposed at a direction substantially perpendicular to a flow of the fluid for detecting the temperature of the fluid and outputting lateral side temperature signals, said fluid-measuring device comprising:

a heater controller for intermittently driving the heater for a measuring interval from a start of measuring the flow rate to the end of measuring;

a lateral side temperature signal upon non-driving receiving member for receiving a lateral side temperature signal outputted from the lateral side temperature sensor whenever the heater stops driving by a control of the heater controller as a lateral side temperature signal upon non-driving;

a lateral side temperature signal upon driving receiving member for receiving a lateral side temperature signal outputted from the lateral side temperature sensor in response to the driving of the heater controlled by the heater controller after the lateral side temperature signal upon non-driving receiving member receives the lateral side temperature signal upon non-driving as a lateral side temperature signal upon driving corresponding to the lateral side temperature signal upon non-driving received by the lateral side temperature signal upon non-driving receiving member;

a physical properties data detecting member for detecting physical properties data indicating physical properties of the fluid corresponding to the thermal profile in the substantially perpendicular direction on the basis of the lateral side temperature signal upon non-driving received by the lateral side temperature signal upon non-driving receiving member and the lateral side temperature signal upon driving received by the lateral side temperature signal upon driving receiving member;

a temperature signal receiving member for receiving the upstream side temperature signal outputted by the upstream side temperature sensor and the downstream side temperature signal outputted by the downstream side temperature sensor corresponding to the lateral side temperature signal upon driving received by the lateral side temperature signal upon driving receiving member when the heater is driven by a control of the heater controller;

a correcting member for correcting the upstream and downstream side temperature signals received by the temperature signal receiving member on the basis of the physical properties data detected by the physical properties data detecting member; and a flow rate calculating member for detecting the temperature profile varied corresponding to the velocity of the fluid on the basis of the upstream and downstream side temperature signals corrected by the correcting member and calculating the flow rate of the fluid on the basis of the detected temperature profile.

2. The fluid-measuring device as claimed in claim 1 further comprising a temperature signal upon non-driving receiving member for receiving the upstream side temperature signal outputted by the upstream side temperature sensor and the downstream side temperature signal outputted by the downstream side temperature sensor corresponding to the lateral side temperature signal upon non-driving received by the lateral side temperature signal upon non-driving receiving member when the heater is not driven by the control of the heater controller, wherein the correcting member corrects the upstream and downstream side temperature signals received by the temperature signal receiving member on the basis of the upstream and downstream side temperature signals received by the temperature signal upon non-driving receiving member, and corrects the corrected upstream and downstream side temperature signals on the basis of the physical properties data detected by the physical properties data detecting member.

3. A method for measuring a flow rate of the fluid with a flow sensor, said flow sensor including:

a heater for generating a specific temperature profile by heating the fluid flowing in a flow path;

an upstream side temperature sensor for detecting a temperature of the fluid at the upstream side of the flow path with respect to the heater, and outputting an upstream side temperature signal;

a downstream side temperature sensor for detecting the temperature of the fluid at the downstream side of the flow path with respect to the heater, and outputting an downstream side temperature signal; and a lateral side temperature sensor disposed substantially perpendicular to a flow direction of the fluid for detecting the temperature of the fluid and outputting the lateral side temperature signal, said fluid-measuring method comprising the steps of:

controlling the heater intermittently driving during a measuring period from a start of the measurement of the flow rate to an end, receiving the lateral side temperature signal outputted from the lateral side temperature sensor as a lateral side temperature signal upon non-driving during the measuring period, whenever the heater stops driving;

receiving the lateral side temperature signal outputted from the lateral side temperature sensor in response to the driving of the heater as a lateral side temperature signal upon driving corresponding to the lateral side temperature signal upon non-driving;

receiving the upstream side temperature signal outputted from the upstream side temperature sensor and the downstream side temperature signal outputted from the downstream side temperature sensor corresponding to the lateral side temperature signal upon driving;

detecting a physical properties data for indicating physical properties of the fluid in the substantially perpendicular direction in response to the temperature profile on the basis of the lateral side temperature signal upon non-driving the lateral side temperature signal upon driving;

correcting the upstream and downstream side temperature signals on the basis of the physical properties data;

detecting the temperature profile changed corresponding to the velocity of the fluid on the basis of the corrected upstream and downstream side temperature signals; and calculating the flow rate of the fluid on the basis of the detected temperature profile.

* * * * *